United States Patent [19]

Handte et al.

[11] Patent Number: 4,482,373
[45] Date of Patent: Nov. 13, 1984

[54] BENZOXAZOLYLOXY PHENOXY ESTERS AND USE AS MONOCOTYLEDONOUS WEED GRASS HERBICIDES

[75] Inventors: Reinhard Handte; Karl Matterstock, both of Hofheim am Taunus; Hermann Bieringer, Eppstein; Helmut Köcher, Hofheim am Taunus, all of Fed. Rep. of Germany

[73] Assignee: Hoechst Aktiengesellschaft, Frankfurt am Main, Fed. Rep. of Germany

[21] Appl. No.: 529,923

[22] Filed: Sep. 7, 1983

Related U.S. Application Data

[63] Continuation of Ser. No. 137,953, Apr. 7, 1980, abandoned.

[30] Foreign Application Priority Data

Apr. 9, 1979 [DE] Fed. Rep. of Germany ....... 2914300

[51] Int. Cl.³ ................... A01N 43/76; C07D 263/58
[52] U.S. Cl. ........................................ 71/88; 548/221
[58] Field of Search ............... 548/165, 221; 71/90, 71/88

[56] References Cited

U.S. PATENT DOCUMENTS

| 3,439,018 | 4/1969 | Brookes et al. | 562/435 |
| 3,954,442 | 5/1976 | Becker et al. | 71/100 |
| 4,130,413 | 12/1978 | Handte et al. | 71/90 |
| 4,227,009 | 10/1980 | Koch et al. | 71/108 |

FOREIGN PATENT DOCUMENTS

| 0005501 | 11/1979 | European Pat. Off. | 71/88 |
| 1009421 | 5/1957 | Fed. Rep. of Germany | 71/108 |
| 2830066 | 1/1980 | Fed. Rep. of Germany | 71/90 |
| 2046753 | 11/1980 | United Kingdom | 71/90 |
| 1579201 | 11/1980 | United Kingdom | |

Primary Examiner—Glennon H. Hollrah
Assistant Examiner—D. B. Springer
Attorney, Agent, or Firm—Curtis, Morris & Safford

[57] ABSTRACT

Compounds of formula

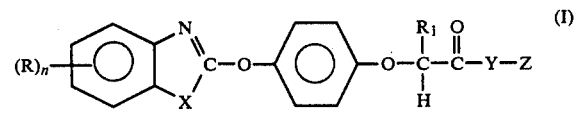

wherein R is halogen, $CF_3$, $NO_2$, CN, ($C_1$-$C_4$)alkyl or ($C_1$-$C_4$)-alkoxy, n is zero or 1, X is O, S, NH, or N-($C_1$-$C_4$)alkyl, Y is O or S, $R^1$ is H or ($C_1$-$C_4$)alkyl and Z is, among others, a cyanalkyl, (subst.) carbalkoxyalkyl, (subst.) carbalkoxyphenyl, sulfoxyalkyl or oxime group, are selective herbicides active especially against weed grasses.

4 Claims, No Drawings

BENZOXAZOLYLOXY PHENOXY ESTERS AND USE AS MONOCOTYLEDONOUS WEED GRASS HERBICIDES

This application is a continuation of application Ser. No. 137,953 filed Apr. 7, 1980 now abandoned.

This invention relates to novel, heterocyclically substituted 4-oxyphenoxyalkane-carboxylic acid derivatives of the formula I

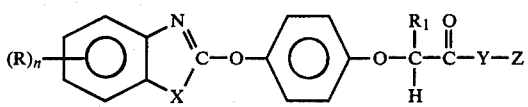

in which
R is halogen, $CF_3$, $NO_2$, CN, $(C_1-C_4)$alkyl or $C_1-C_4$-alkoxy,
X is O, S, NH, or N—$(C_1-C_4)$alkyl,
Y is O or S,
$R^1$ is H or $(C_1-C_4)$alkyl,
Z is a group of the formula

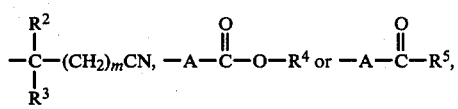

or, in the case of Y being O also a group of the formula

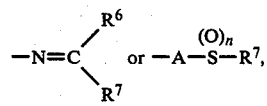

n is zero or 1 or 2
m is zero or 1,
A is $(C_1-C_3)$alkylene which is optionally mono- or disubstituted by $(C_1-C_4)$alkyl or monosubstituted by —$COCH_3$, —$COOR^4$ or phenyl which in turn may be mono- or disubstituted by $(C_1-C_4)$-alkyl, halogen and/or $NO_2$,
$R^2$ and $R^3$ are H or $(C_1-C_4)$alkyl,
$R^4$ is H, $(C_1-C_{12})$alkyl which is optionally substituted by one or two F, Cl, Br and/or by one OH, $(C_1-C_6)$alkoxy or $(C_1-C_6)$alkoxy-$(C_2-C_6)$alkoxy, furthermore, $R^4$ is $(C_5-C_6)$cycloalkyl, halo$(C_5-C_6)$cycloalkyl, $(C_3-C_6)$alkenyl, $(C_5-C_6)$cycloalkenyl, $(C_3-C_6)$alkinyl, furfuryl, tetrahydrofurfuryl, or a cation equivalent of an organic or inorganic base,
$R^5$ is $(C_1-C_4)$alkyl,
$R^6$ is H or $(C_1-C_4)$alkyl and
$R^7$ is H, $(C_1-C_4)$alkyl, $(C_2-C_6)$alkenyl, $(C_2-C_6)$alkinyl, or phenyl with the proviso that one of the radicals $R^6$ and $R^7$ is other than hydrogen.

If n is 2 the radicals R can be identical or different. Alkyl, alkenyl and alkinyl of the radicals R to $R^5$ can be linear or branched.

Preferred compounds of the formula I are those in which R is halogen, $CF_3$, $NO_2$ and CN; n is zero or 1; X is O or S; $R^1$ is $CH_3$ and Y is O. Halogen preferably denotes chlorine or bromine. Z is preferably cyanoethyl or a radical of the formula

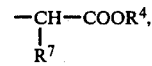

in which $R^4$ is preferably $(C_1-C_4)$alkyl and $R^7$ is H or $(C_1-C_3)$alkyl.

If $R^1$ is other than hydrogen, the compounds of the formula have an asymmetric center and are normally obtained as racemates. The invention also includes the isolated optical antipodes and preferably their d-forms.

It is another object of the present invention to provide a process for the manufacture of the compounds of the formula I which comprises reacting
(a) a compound of the formula II

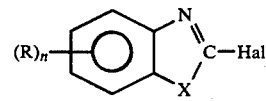

in which Hal is a halogen atom, with a compound of the formula III

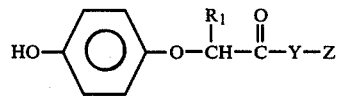

or
(b) a compound of the formula

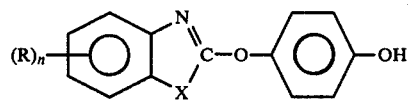

with a compound of the formula V

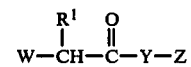

in which W is halogen, preferably chlorine or bromine, or the tosyl radical, or
(c) a compound of the formula

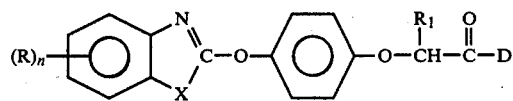

with a compound of the formula B—Z (VII) in which either D or B is halogen and the other is the group —YH.

The reactions according to (a) to (c) are carried out in a manner known per se either in the presence of acid-binding agents or the starting compounds III, IV or VI (VII) are used in the form of their salts. Conventional processes are described, for example, in U.S. Pat. No. 4,130,413, EP-OS 0,002,246 and DE-OS 2,623,558.

The starting compounds of formula II to VII are known or can be prepared by known processes. When optically active starting compounds of the formula III, V or VI in which $R^1$ is not hydrogen ($CH_3$ being preferred) are used, optical isomers of the compounds of the invention (the d-form being preferred) can be prepared in a high optical purity.

The compounds of the formula I according to the invention are very effective in pre-emergence and post-emergence application against a broad range of annual and perennial monocotyledonous weeds and, simultaneously, they are excellently tolerated by dicotyledonous crop plants and some cereals. Hence, they can be used for selectively combating annual and perennial monocotyledonous weeds in crops, shrubberies, plantations and the like. Weed grasses that can be controlled are, for example, wild oat (Avena), annual blackgrass (Alopecurus spp.), meadow grass (Poa spp.), raygrass (Lolium spp.) annual and perennial wild millets (Echinochloa spp., Setaria spp., Digitaria spp., Panicum spp., Sorghum spp.), Bermuda grass (Cynodon spp.) and couch grass (Agropyron spp.).

It is, therefore, a further object of the present invention to provide herbicidal compositions containing a carrier and as active ingredient, a herbicidally effective amount of a compound of the formula I.

The compositions of the invention contain preferably from 2 to 95% of the active compounds of the formula I. They can be formulated as wettable powders, emulsifiable concentrates, sprayable solutions, dusts or granules.

Wettable powders are formulations which are uniformly dispersible in water and which, in addition to the active compound, diluents or inert materials also contain wetting agents, for example, polyoxyethylated alkylphenols, polyoxyethylated oleylamines or stearylamines, alkylsulfonates or alkylphenylsulfonates, and dispersing agents, for example sodium ligninsulfonates, sodium 2,2'-dinaphthylmethane-6,6'-disulfonate, or the sodium salt of oleyl-methyltaurine.

Emulsifiable concentrates are obtained by dissolving the active compound in an organic solvent, for example, butanol, cyclohexanone, dimethylformamide, xylene or even higher-boiling aromatics and by adding a non-ionic wetting agent, for example a polyoxyethylated alkylphenol or a polyoxyethylated oleyl or stearyl amine.

Dusting agents are obtained by grinding the active compound with finely divided solids, for example talc, natural clays, such as kaolin, bentonite, pyrophillite or diatomaceous earth.

Granules can be manufactured either by spraying the active compound onto adsorbent, granular inert material or by applying active compound concentrates by means of adhesives, for example polyvinyl alcohol, sodium polyacrylate or even mineral oils, onto the surfaces of carriers, such as sand, kaolinites or granular inert material. Suitable formulations can also be manufactured by the customary methods of manufacture of fertilizer granules, if desired in admixture with fertilizers.

In the herbicidal compositions the concentrations of the active compounds in the commercial formulations can vary. In wettable powders, the active compound concentration varies, for example, between about 10 and 95%, the remainder consisting of one or more of the abovementioned formulation additives. In the case of emulsifiable concentrates, the active compound concentration is about 10% to 80%. Dust formulations usually contain 5–20% of active compound, and sprayable solutions about 2–20%. In the case of granules, the active compound content in part depends on whether the active compound is in a liquid or solid form and what granulating auxiliaries, fillers and the like are used.

If necessary or desired the commercial concentrates may be diluted prior to application in the usual manner, for example by means of water in the case of wettable powders and emulsifiable concentrates. Dust, granules and sprayable solutions are generally ready for use without further dilution. The amount of active ingredient necessary for obtaining the desired result depends on external conditions such as temperature, humidity and the like. It is generally from 0.05 to 10.0 kg/ha or more of active substance, preferably from 0.1 to 5 kg/ha.

The active compounds according to the invention can be combined with other herbicides and soil insecticides.

The following examples illustrate the invention.

EXAMPLES OF FORMULATION

EXAMPLE A An emulsifiable concentrate is obtained from 15 parts by weight of active substance
75 parts by weight of cyclohexanone as solvent and
10 parts by weight of oxethylated nonyl phenol (10 EO) as emulsifier.

EXAMPLE B

A wettable powder which is easily dispersible in water is obtained by mixing
25 parts by weight of active substance,
64 parts by weight of quartz containing kaolin as inert material,
10 parts by weight of potassium lignosulfonate and
1 part by weight of sodium oleyl-methyl-taurine as wetting and dispersing agent and grinding the mixture in a pin mill.

EXAMPLE C

A dusting powder is obtained by mixing
10 parts by weight of active substance and
90 parts by weight of talc as inert material and comminuting the mixture in a hammer mill.

EXAMPLE D

A granular formulation consists, for example, of about 2 to 15 parts by weight of active substance and inert granular carrier materials such as attapulgite, pumice and quartz sand.

EXAMPLES OF PREPARATION

EXAMPLE 1

2-[4-(2-Benzthiazolyloxy)-phenoxy]-propionyl-lactic acid methyl ester 48.6 g of 4-(2-benzthiazolyloxy)-phenol, 33.1 g of potassium carbonate and 50.2 g of 2-bromopropionyl-lactic acid methyl ester in 250 cc of acetonitrile are refluxed for 8 hours. After cooling the salt precipitate is filtered off and the acetonitrile is distilled off. The residue is fraction-distilled, yielding 68 g (82.5% of theory) of 2-[4-(2-benzthiazolyloxy)-phenoxy]-propionyl-lactic acid methyl ester, b.p. 218° to 220° C./0.01 mbar.

BENZOXAZOLYLOXY PHENOXY ESTERS AND USE AS MONOCOTYLEDONOUS WEED GRASS HERBICIDES

This application is a continuation of application Ser. No. 137,953 filed Apr. 7, 1980 now abandoned.

This invention relates to novel, heterocyclically substituted 4-oxyphenoxyalkane-carboxylic acid derivatives of the formula I

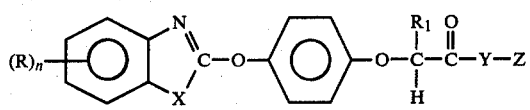

in which
R is halogen, $CF_3$, $NO_2$, CN, $(C_1-C_4)$alkyl or $C_1-C_4$-alkoxy,
X is O, S, NH, or N—$(C_1-C_4)$alkyl,
Y is O or S,
$R^1$ is H or $(C_1-C_4)$alkyl,
Z is a group of the formula

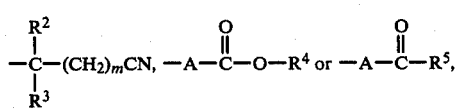

or, in the case of Y being O also a group of the formula

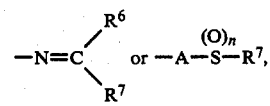

n is zero or 1 or 2
m is zero or 1,
A is $(C_1-C_3)$alkylene which is optionally mono- or disubstituted by $(C_1-C_4)$alkyl or monosubstituted by —$COCH_3$, —$COOR^4$ or phenyl which in turn may be mono- or disubstituted by $(C_1-C_4)$-alkyl, halogen and/or $NO_2$,
$R^2$ and $R^3$ are H or $(C_1-C_4)$alkyl,
$R^4$ is H, $(C_1-C_{12})$alkyl which is optionally substituted by one or two F, Cl, Br and/or by one OH, $(C_1-C_6)$alkoxy or $(C_1-C_6)$alkoxy-$(C_2-C_6)$alkoxy, furthermore, $R^4$ is $(C_5-C_6)$cycloalkyl, halo$(C_5-C_6)$cycloalkyl, $(C_3-C_6)$alkenyl, $(C_5-C_6)$cycloalkenyl, $(C_3-C_6)$alkinyl, furfuryl, tetrahydrofurfuryl, or a cation equivalent of an organic or inorganic base,
$R^5$ is $(C_1-C_4)$alkyl,
$R^6$ is H or $(C_1-C_4)$alkyl and
$R^7$ is H, $(C_1-C_4)$alkyl, $(C_2-C_6)$alkenyl, $(C_2-C_6)$alkinyl, or phenyl with the proviso that one of the radicals $R^6$ and $R^7$ is other than hydrogen.

If n is 2 the radicals R can be identical or different. Alkyl, alkenyl and alkinyl of the radicals R to $R^5$ can be linear or branched.

Preferred compounds of the formula I are those in which R is halogen, $CF_3$, $NO_2$ and CN; n is zero or 1; X is O or S; $R^1$ is $CH_3$ and Y is O. Halogen preferably denotes chlorine or bromine. Z is preferably cyanoethyl or a radical of the formula

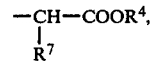

in which $R^4$ is preferably $(C_1-C_4)$alkyl and $R^7$ is H or $(C_1-C_3)$alkyl.

If $R^1$ is other than hydrogen, the compounds of the formula have an asymmetric center and are normally obtained as racemates. The invention also includes the isolated optical antipodes and preferably their d-forms.

It is another object of the present invention to provide a process for the manufacture of the compounds of the formula I which comprises reacting
(a) a compound of the formula II

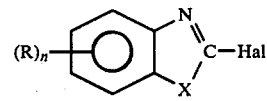

in which Hal is a halogen atom, with a compound of the formula III

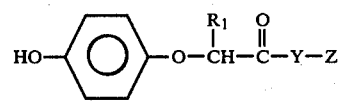

or
(b) a compound of the formula

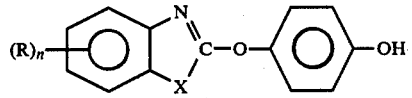

with a compound of the formula V

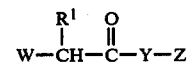

in which W is halogen, preferably chlorine or bromine, or the tosyl radical, or
(c) a compound of the formula

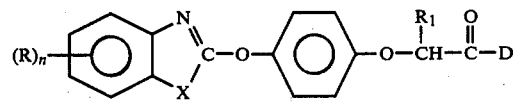

with a compound of the formula B—Z (VII) in which either D or B is halogen and the other is the group —YH.

The reactions according to (a) to (c) are carried out in a manner known per se either in the presence of acid-binding agents or the starting compounds III, IV or VI (VII) are used in the form of their salts. Conventional processes are described, for example, in U.S. Pat. No. 4,130,413, EP-OS 0,002,246 and DE-OS 2,623,558.

The starting compounds of formula II to VII are known or can be prepared by known processes. When optically active starting compounds of the formula III, V or VI in which $R^1$ is not hydrogen ($CH_3$ being preferred) are used, optical isomers of the compounds of the invention (the d-form being preferred) can be prepared in a high optical purity.

The compounds of the formula I according to the invention are very effective in pre-emergence and post-emergence application against a broad range of annual and perennial monocotyledonous weeds and, simultaneously, they are excellently tolerated by dicotyledonous crop plants and some cereals. Hence, they can be used for selectively combating annual and perennial monocotyledonous weeds in crops, shrubberies, plantations and the like. Weed grasses that can be controlled are, for example, wild oat (Avena), annual blackgrass (Alopecurus spp.), meadow grass (Poa spp.), raygrass (Lolium spp.) annual and perennial wild millets (Echinochloa spp., Setaria spp., Digitaria spp., Panicum spp., Sorghum spp.), Bermuda grass (Cynodon spp.) and couch grass (Agropyron spp.).

It is, therefore, a further object of the present invention to provide herbicidal compositions containing a carrier and as active ingredient, a herbicidally effective amount of a compound of the formula I.

The compositions of the invention contain preferably from 2 to 95% of the active compounds of the formula I. They can be formulated as wettable powders, emulsifiable concentrates, sprayable solutions, dusts or granules.

Wettable powders are formulations which are uniformly dispersible in water and which, in addition to the active compound, diluents or inert materials also contain wetting agents, for example, polyoxyethylated alkylphenols, polyoxyethylated oleylamines or stearylamines, alkylsulfonates or alkylphenylsulfonates, and dispersing agents, for example sodium ligninsulfonates, sodium 2,2'-dinaphthylmethane-6,6'-disulfonate, or the sodium salt of oleyl-methyltaurine.

Emulsifiable concentrates are obtained by dissolving the active compound in an organic solvent, for example, butanol, cyclohexanone, dimethylformamide, xylene or even higher-boiling aromatics and by adding a non-ionic wetting agent, for example a polyoxyethylated alkylphenol or a polyoxyethylated oleyl or stearyl amine.

Dusting agents are obtained by grinding the active compound with finely divided solids, for example talc, natural clays, such as kaolin, bentonite, pyrophillite or diatomaceous earth.

Granules can be manufactured either by spraying the active compound onto adsorbent, granular inert material or by applying active compound concentrates by means of adhesives, for example polyvinyl alcohol, sodium polyacrylate or even mineral oils, onto the surfaces of carriers, such as sand, kaolinites or granular inert material. Suitable formulations can also be manufactured by the customary methods of manufacture of fertilizer granules, if desired in admixture with fertilizers.

In the herbicidal compositions the concentrations of the active compounds in the commercial formulations can vary. In wettable powders, the active compound concentration varies, for example, between about 10 and 95%, the remainder consisting of one or more of the abovementioned formulation additives. In the case of emulsifiable concentrates, the active compound concentration is about 10% to 80%. Dust formulations usually contain 5-20% of active compound, and sprayable solutions about 2-20%. In the case of granules, the active compound content in part depends on whether the active compound is in a liquid or solid form and what granulating auxiliaries, fillers and the like are used.

If necessary or desired the commercial concentrates may be diluted prior to application in the usual manner, for example by means of water in the case of wettable powders and emulsifiable concentrates. Dust, granules and sprayable solutions are generally ready for use without further dilution. The amount of active ingredient necessary for obtaining the desired result depends on external conditions such as temperature, humidity and the like. It is generally from 0.05 to 10.0 kg/ha or more of active substance, preferably from 0.1 to 5 kg/ha.

The active compounds according to the invention can be combined with other herbicides and soil insecticides.

The following examples illustrate the invention.

EXAMPLES OF FORMULATION

EXAMPLE A An emulsifiable concentrate is obtained from 15 parts by weight of active substance
75 parts by weight of cyclohexanone as solvent and
10 parts by weight of oxethylated nonyl phenol (10 EO) as emulsifier.

EXAMPLE B

A wettable powder which is easily dispersible in water is obtained by mixing
25 parts by weight of active substance,
64 parts by weight of quartz containing kaolin as inert material,
10 parts by weight of potassium lignosulfonate and
1 part by weight of sodium oleyl-methyl-taurine as wetting and dispersing agent and grinding the mixture in a pin mill.

EXAMPLE C

A dusting powder is obtained by mixing
10 parts by weight of active substance and
90 parts by weight of talc as inert material and comminuting the mixture in a hammer mill.

EXAMPLE D

A granular formulation consists, for example, of about 2 to 15 parts by weight of active substance and inert granular carrier materials such as attapulgite, pumice and quartz sand.

EXAMPLES OF PREPARATION

EXAMPLE 1

2-[4-(2-Benzthiazolyloxy)-phenoxy]-propionyl-lactic acid methyl ester 48.6 g of 4-(2-benzthiazolyloxy)-phenol, 33.1 g of potassium carbonate and 50.2 g of 2-bromopropionyl-lactic acid methyl ester in 250 cc of acetonitrile are refluxed for 8 hours. After cooling the salt precipitate is filtered off and the acetonitrile is distilled off. The residue is fraction-distilled, yielding 68 g (82.5% of theory) of 2-[4-(2-benzthiazolyloxy)-phenoxy]-propionyl-lactic acid methyl ester, b.p. 218° to 220° C./0.01 mbar.

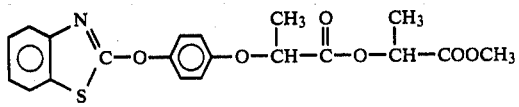

EXAMPLE 2

2-[4-(5-Chloro-2-benzoxazolyloxy)-phenoxy]-propionyl-glycolic acid methyl ester 25.4 g of 2-(4-hydroxyphenoxy)-propionyl-glycolic acid methyl ester and 16.6 g of potassium carbonate in 180 cc of acetonitrile are refluxed for 1 hour to form a salt. After addition of 20 g of 2,5-dichlorobenzoxazole, the mixture is refluxed for 10 hours. The salt is filtered off at 60° C. and the acetonitrile is distilled off. The residue is freed in vacuo from volatile residues. 34 g (84.8% of theory) of 2-[4-(5-chloro-2-benzoxazolyloxy)-phenoxy]-propionyl-glycolic acid methyl ester are obtained as a brownish viscous oil, $n_D^{23} = 1.5587$.

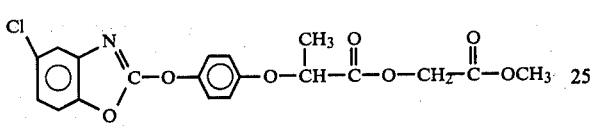

EXAMPLE 3

2-[4-(6-Chloro-2-benzthiazolyloxy)-phenoxy]-propionyl-thioglycolic acid methyl ester 36.8 g or 2-[4-(6-chlorobenzthiazolyloxy)-phenoxy]-propionyl chloride (prepared by reacting 35 g of the free acid with 13.1 g of thionyl chloride in 150 cc of toluene for 8 hours at 80° C.) are added to 150 cc of toluene and a mixture of 12.1 g of triethylamine and 10.6 g of thioglycolic acid methyl ester in 50 cc of toluene is added at 25° to 30° C. The reaction mixture is stirred for a further 2 hours at 50° to 60° C. The mixture is cooled to 25° C. and washed three times with 150 cc of water each. The toluene phase is dried over sodium sulfate, filtered and evaporated to dryness. The residue has completely crystallized after 3 days, yielding 40.5 g (92.7% of theory) of 2-[4-(6-chloro-2-benzthiazolyloxy)-phenoxy]-propionyl-glycolic acid methyl ester. m.p. 104° to 106° C.

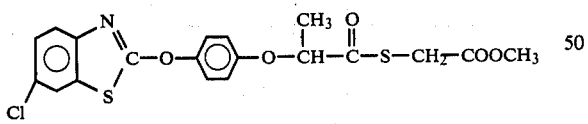

The compounds listed in the following tables are prepared according to the processes of Examples 1 to 3.

TABLE 1

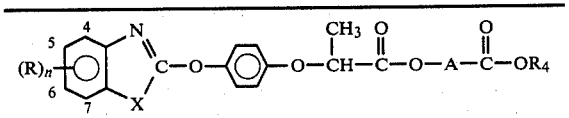

| Example No. | (R)$_n$ | X | R$_4$ | phys. constants |
|---|---|---|---|---|
| | | | | A: $-\overset{CH_3}{\underset{|}{CH}}-$    (1) |

TABLE 1-continued

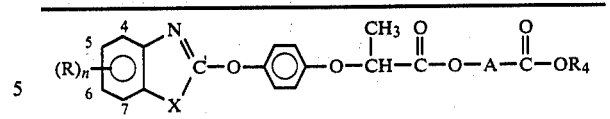

| Example No. | (R)$_n$ | X | R$_4$ | phys. constants |
|---|---|---|---|---|
| 4 | H | O | CH$_3$ | b.p.: 212–215 (0.013 mbar) |
| 5 | 5-Cl | O | C$_2$H$_5$ | $n_D^{27}$: 1.5612 |
| 6 | 6-Cl | O | C$_2$H$_5$ | $n_D^{23}$: 1.5372 |
| 7 | 6-Cl | O | C$_4$H$_9$(iso) | $n_D^{23}$: 1.5296 |
| 8 | 6-Cl | O | CH$_3$ | $n_D^{23}$: 1.5646 |
| 9 | H | S | C$_3$H$_7$ | $n_D^{21}$: 1.5531 |
| 10 | 6-Cl | S | C$_2$H$_5$ | $n_D^{19}$: 1.5731 |
| 11 | 6-Cl | S | CH$_3$ | $n_D^{19}$: 1.6050 |
| 12 | 6-Cl | S | C$_4$H$_9$(iso) | $n_D^{19}$: 1.5516 |
| 13 | 6-Br | S | CH$_3$ | |
| 14 | H | S | C$_2$H$_4$—O—CH$_3$ | |
| 15 | 6-Cl | S | H | $n_D^{20}$: 1.5804 |
| | | | A: $-CH_2-$ | (2) |
| 16 | H | S | CH$_3$ | $n_D^{27}$: 1.5772 |
| 17 | 6-Cl | S | CH$_3$ | $n_D^{22}$: 1.5930 |
| 18 | 6-Cl | S | C$_2$H$_5$ | $n_D^{22}$: 1.5728 |
| 19 | 6-Cl | O | CH$_3$ | $n_D^{30}$: 1.5663 |
| 20 | 6-Cl | O | C$_3$H$_7$ | $n_D^{20}$: 1.5405 |
| | | | A: $-\overset{C_2H_5}{\underset{|}{CH}}-$ | (3) |
| 21 | H | S | CH$_3$ | |
| 22 | 6-Cl | S | C$_2$H$_5$ | |
| 23 | 6-Br | S | CH$_3$ | |
| 24 | 5-Cl | O | C$_3$H$_7$(n) | |
| 25 | 6-Cl | O | CH$_3$ | |

TABLE 2

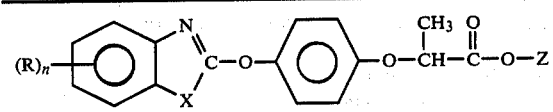

| Example No. | (R)$_n$ | X | Z | physical constants |
|---|---|---|---|---|
| 26 | 6-Cl | S | —CH$_2$—CH$_2$—CN | $n_D^{22}$: 1.5780 |
| 27 | 6-Cl | O | —CH$_2$—CH$_2$—CN | $n_D^{21}$: 1.5217 |
| 28 | 5-Cl | O | —CH$_2$—CH$_2$—CN | $n_D^{27}$: 1.5593 |
| 29 | 6-Br | S | —CH$_2$—CH$_2$—CN | |
| 30 | H | S | $-\overset{CH_3}{\underset{|}{CH}}-CN$ | $n_D^{24}$: 1.5709 |
| 31 | 6-Cl | S | " | $n_D^{32}$: 1.5749 |
| 32 | 6-Cl | O | " | $n_D^{29}$: 1.5712 |
| 33 | 5-Cl | O | " | $n_D^{28}$: 1.5655 |
| 34 | 6-Br | S | " | |
| 34a | 6-Cl | O | —N=C(CH$_3$)$_2$ | m.p. 89.5–90.5° C. |
| 34b | 6-Cl | S | " | m.p. 89.5–90.5° C. |
| 34c | 6-Cl | S | —CH$_2$CH$_2$COCH$_3$ | |
| 34d | 6-Cl | S | —CH$_2$CH$_2$S—C$_2$H$_5$ | |
| 34e | 6-Cl | S | —CH$_2$CH$_2$SO$_2$C$_2$H$_5$ | |

TABLE 3

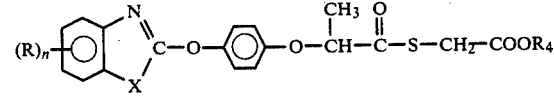

| Example No. | (R)$_n$ | X | R$_4$ | physical constants |
|---|---|---|---|---|
| 35 | 6-Cl | S | C$_2$H$_5$ | $n_D^{22}$: 1.5825 |

TABLE 3-continued

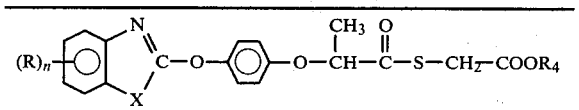

| Example No. | (R)$_n$ | X | R$_4$ | physical constants |
|---|---|---|---|---|
| 36 | H | S | CH$_3$ | n$_D^{27}$: 1.5948 |
| 37 | 5-Cl | O | CH$_3$ | n$_D^{28}$: 1.5630 |
| 38 | 6-Cl | O | C$_2$H$_5$ | n$_D^{20}$: 1.5628 |

TABLE 4

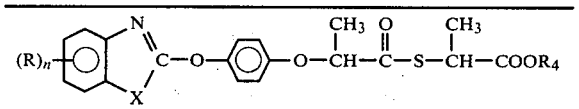

| Example No. | (R)$_n$ | X | R$_4$ | physical constants |
|---|---|---|---|---|
| 39 | 5-Cl | O | CH$_3$ | n$_D^{27}$: 1.5936 |
| 40 | 6-Cl | O | C$_2$H$_5$ | n$_D^{27}$: 1.5913 |
| 41 | H | S | H | n$_D^{27}$: 1.5952 |
| 42 | 6-Cl | S | C$_2$H$_5$ | n$_D^{23}$: 1.5783 |
| 43 | 6-Br | S | CH$_3$ | |

BIOLOGICAL EXAMPLES

EXAMPLE I (Pre-emergence application)

Seeds of grasses were sown in pots and the compounds of the invention formulated as wettable powders or emulsion concentrates were sprayed in different concentrations onto the surface of the soil. The pots were then kept for 4 weeks in the greenhouse. The result of the treatment was evaluated here (and in the following examples) according to the following scheme:
1    0–20% damage
2    20–40% damage
3    40–60% damage
4    60–80% damage
5    80–100% damage The results show that the compounds of the invention have a good effect against annual and in part also perennial weed grasses.

TABLE I

Pre-emergence application
(dosage: 2.4 kg of active substance per hectare)

| Compound of Example | AVF | ALM | SAL | LOM | ECG | AGR | CND |
|---|---|---|---|---|---|---|---|
| 1 | — | 5 | 5 | 5 | 5 | — | — |
| 2 | — | 5 | 5 | 5 | 5 | — | — |
| 7 | 5 | 5 | 5 | 5 | 5 | — | — |
| 8 | 5 | 5 | 5 | 5 | 5 | — | — |
| 9 | 4 | 5 | 5 | 5 | 5 | 5 | — |
| 10 | 5 | 5 | 5 | 5 | 5 | 5 | — |
| 11 | 5 | 5 | 5 | 5 | 5 | 5 | — |
| 12 | 5 | 5 | 5 | 5 | 5 | 5 | 3 |
| 15 | 5 | 5 | 5 | 5 | 5 | 5 | — |
| 16 | 3 | 5 | 5 | 5 | 5 | — | — |
| 17 | 5 | 5 | 5 | 5 | 5 | 5 | — |
| 18 | 5 | 5 | 5 | 5 | 5 | 5 | — |
| 19 | 5 | 5 | 5 | 5 | 5 | — | 5 |
| 26 | 5 | 5 | 5 | 5 | 5 | 5 | 4 |
| 27 | 5 | 5 | 5 | 5 | 5 | — | 5 |
| 30 | 4 | 5 | 5 | 5 | 5 | 5 | — |
| 31 | 5 | 5 | 5 | 5 | 5 | 5 | — |
| 32 | 5 | 5 | 5 | 5 | 5 | — | 5 |
| 33 | 5 | 5 | 5 | 4 | 5 | — | — |
| 35 | 5 | 5 | 5 | 5 | 5 | 5 | — |
| 36 | 4 | 5 | 5 | 5 | 5 | — | — |
| 38 | 5 | 5 | 5 | 5 | 5 | — | 5 |
| 34a | 5 | 5 | 5 | 5 | 5 | — | 4 |
| 34b | 5 | 5 | 5 | 5 | 5 | 5 | — |

ALM Alopecurus
SAL Setaria
LOM Lolium
ECG Echinochloa
AGR Agropyron
CND Cynodon

EXAMPLE II (Post-emergence application)

Seeds of grasses were sown in pots and the plants were grown in the greenhouse. 3 Weeks after sowing the compounds of the invention formulated as wettable powders or emulsion concentrates were sprayed onto the plants in different concentrations and after a standing time in the greenhouse of 4 weeks the effect of the active substances was evaluated visually.

The compounds of the invention had a good herbicidal effect against a broad range of annual weed grasses. Some compounds also controlled perennial weed grasses such as Cynodon dactylon, Sorghum halepense and Agropyron repens.

TABLE II

Post-ermergence effect
(dosage: 2.4 kg of active substance per hectare)

| Compound of Example | ALM | SAL | LOM | ECG |
|---|---|---|---|---|
| 12 | 5 | 5 | 5 | 5 |
| 11 | 5 | 5 | 5 | 5 |
| 10 | 5 | 5 | 5 | 5 |
| 15 | 5 | 5 | 5 | 5 |
| 17 | 5 | 5 | 5 | 5 |
| 18 | 5 | 5 | 5 | 5 |
| 35 | 5 | 5 | 5 | 5 |
| 26 | 5 | 5 | 5 | 5 |
| 1 | 5 | 3 | 5 | 5 |
| 16 | 5 | 4 | 5 | 5 |
| 36 | 5 | 3 | 5 | 5 |

EXAMPLE III (Crop plant tolerance)

Seeds of various crop plants were sown in pots. Some of the pots were treated immediately with compounds of the invention whereas others were kept in the greenhouse until the 2 to 3 leaf-stage of the plants. The plants were then sprayed with the compounds of the invention.

The results evaluated 4 to 5 weeks after application show that the compounds of the invention did no harm or little harm only to dicotyledonous crop plants even if applied in a concentration of 2.4 kg per hectare. Moreover, some of the substances did not damage cereals such as barley, sorghum, maize, wheat and rice. This demonstrates the high selectivity of the invention compounds.

TABLE III

Crop tolerance (damage in %) dosage 2.4 kg of active substance per hectare

| Compound of Example | pre-emergence | | | post-emergence | |
|---|---|---|---|---|---|
| | sugar beet | rape | soybean | sugar beet | soybean |
| 12 | 0 | 0 | 0 | 0 | 0 |
| 11 | 0 | 0 | 0 | 0 | 0 |
| 10 | 0 | 0 | 0 | 0 | 0 |
| 15 | 0 | 0 | 5 | 0 | 0 |
| 17 | 0 | 0 | 0 | 0 | 0 |
| 16 | 0 | 0 | 0 | 0 | 0 |
| 31 | 0 | 0 | 0 | 0 | 3 |
| 8 | 0 | 0 | 0 | 0 | 0 |
| 27 | 0 | 0 | 0 | 0 | 0 |
| 30 | 0 | 0 | 2 | 0 | 0 |
| 33 | 0 | 0 | 0 | 0 | 0 |

What is claimed is:

1. A compound of the formula

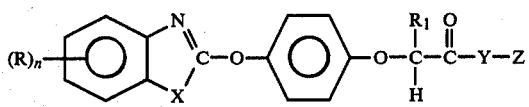

wherein

R is halogen, $CF_3$, $NO_2$, $CN(C_1-C_4)$ alkyl or $(C_1-C_4)$ alkoxy;

n is 0, 1 or 2;

X is O;

Y is O or S;

$R^1$ is H or $(C_1-C_4)$ alkyl;

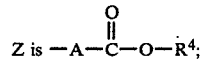

A is $(C_1-C_3)$ alkylene and $R^4$ is H or unsubstituted $(C_1-C_{12})$ alkyl.

2. A compound as claimed in claim 1 having the formula

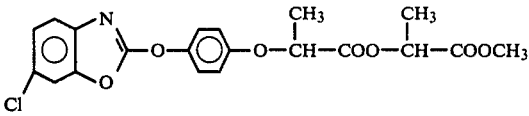

3. Herbicidal composition containing, in addition to the usual additives and formulation auxiliaries, a herbicidally effective amount of a benzoxazole as defined in claim 1.

4. Method of combating monocotyledonous weed grasses which comprises applying to the locus of the undesired plant growth a herbicidally effective amount of a benzoxazole as defined in claim 1.

* * * * *